United States Patent
Yokoi et al.

(10) Patent No.: US 12,152,269 B2
(45) Date of Patent: Nov. 26, 2024

(54) EXAMINATION SYSTEM, EXAMINATION DEVICE, AND EXAMINATION METHOD FOR TESTING SAMPLE QUALITY PRIOR TO BIOMARKER DETECTION

(71) Applicant: HITACHI, LTD., Tokyo (JP)

(72) Inventors: Takahide Yokoi, Tokyo (JP); Masataka Shirai, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 1024 days.

(21) Appl. No.: 15/738,234

(22) PCT Filed: Jun. 24, 2015

(86) PCT No.: PCT/JP2015/068114
§ 371 (c)(1),
(2) Date: Dec. 20, 2017

(87) PCT Pub. No.: WO2016/207986
PCT Pub. Date: Dec. 29, 2016

(65) Prior Publication Data
US 2018/0195105 A1  Jul. 12, 2018

(51) Int. Cl.
| | |
|---|---|
| *G16H 10/40* | (2018.01) |
| *C12M 1/34* | (2006.01) |
| *C12Q 1/02* | (2006.01) |
| *C40B 40/06* | (2006.01) |
| *G01N 1/00* | (2006.01) |
| *G01N 15/1433* | (2024.01) |
| *G01N 35/00* | (2006.01) |
| *G16B 30/00* | (2019.01) |
| *G16B 50/00* | (2019.01) |
| *G01N 1/28* | (2006.01) |
| *G01N 1/31* | (2006.01) |
| *G01N 15/10* | (2024.01) |

(52) U.S. Cl.
CPC .............. *C12Q 1/02* (2013.01); *C12M 1/34* (2013.01); *C40B 40/06* (2013.01); *G01N 1/00* (2013.01); *G01N 15/1433* (2024.01); *G01N 35/00603* (2013.01); *G16B 30/00* (2019.02); *G16B 50/00* (2019.02); *G16H 10/40* (2018.01); *G01N 1/2813* (2013.01); *G01N 1/31* (2013.01); *G01N 2015/1006* (2013.01); *G01N 2035/0094* (2013.01)

(58) Field of Classification Search
CPC ............ C12Q 1/02; C12M 1/34; C40B 40/06; G16H 10/40
See application file for complete search history.

(56) References Cited

U.S. PATENT DOCUMENTS

| | | | |
|---|---|---|---|
| 2014/0329917 A1 | 11/2014 | Marienfeld et al. | |
| 2015/0003713 A1 | 1/2015 | Duann et al. | |

FOREIGN PATENT DOCUMENTS

| | | | | |
|---|---|---|---|---|
| CN | 104251850 A | 12/2014 | | |
| CN | 104428677 A | 3/2015 | | |
| GB | 2537875 A | * | 11/2016 | ........... A61B 5/0075 |

OTHER PUBLICATIONS

Gurcan, M.N., Boucheron, L.E., Can, A., Madabhushi, A., Rajpoot, N.M. and Yener, B. Histopathological image analysis: A review. IEEE Reviews in Biomedical Engineering, 2, pp. 147-171. (Year: 2009).*
Extended European Search Report for the related European Application No. 15896308.2, mailed on Jan. 9, 2019; 9 pages.
Mattsson et al., " Detection of Genetic Alterations by ImmunoFISH Analysis of Whole Cells Extracted from Routine Biopsy Material", Journal of Molecular Diagnostics, Sep. 1, 2007, 11 pages, vol. 9, No. 4.
Taniguchi, K., et al., "Quantitative analysis of gene expression in a single cell by qPCR", Nature Method, pp. 503-506, (2009), vol. 6, No. 7.
First Office Action for related Chinese Application No. 201580080692. 8, mailed on Aug. 18, 2020; English translation provided (17 pages).

* cited by examiner

*Primary Examiner* — Kaitlyn L Minchella
*Assistant Examiner* — Janna Nicole Schultzhaus
(74) *Attorney, Agent, or Firm* — Procopio, Cory, Hargreaves & Savitch LLP (57) ABSTRACT

The present invention optically obtains characteristic values of a plurality of biological samples from a specimen; compares the characteristic values with examination information associated with the same specimen obtained in advance; and calculates an indicator to determine, based on a result of the comparison, whether a process is continued to genetic analysis of the biological samples or a re-preparation of samples from the same specimen is performed. By this method, it is possible to achieve more reliable biomarker detection by ensuring validity through appropriate selection of test samples while reducing cost, effort, and time for analysis in single cell analysis or analysis of a group of a small number of cells.

3 Claims, 5 Drawing Sheets

FIG. 1

|  | JUDGMENT RESULTS | REFERENCE VALUES | EXAMINATION RESULTS FOR SECOND TEST SAMPLE |
|---|---|---|---|
| [PATHOLOGICAL SUITABILITY JUDGMENT] | | | |
| NUMBER OF CANCER CELLS | SUITABLE | x1 | x2 |
| PERCENTAGE OF CANCER CELLS | SUITABLE | y1 | y2 |
| STAGING | SUITABLE | z1 | z2 |
| [CRITERIA FOR JUDGING TEST METHOD SUITABILITY] | | | |
| SAMPLE IMMOBILIZATION METHOD | SUITABLE | FROZEN | FROZEN |
| SAMPLE STORAGE TEMPERATURE | SUITABLE | A1 to A2 °C | a °C |
| TEST SAMPLE SIZE | SUITABLE | B1 to B2 mm$^2$ | b mm$^2$ |

FIG. 2

| | JUDGMENT RESULTS | REFERENCE VALUES | EXAMINATION RESULTS FOR SECOND TEST SAMPLE | EVALUATION RESULTS FOR INDIVIDUAL CELLS |
|---|---|---|---|---|
| [PATHOLOGICAL SUITABILITY JUDGMENT] | | | | |
| NUMBER OF CANCER CELLS | SUITABLE | x1 | x2 | – |
| PERCENTAGE OF CANCER CELLS | SUITABLE | y1 | y2 | – |
| STAGING | SUITABLE | z1 | z2 | – |
| [CRITERIA FOR JUDGING TEST METHOD SUITABILITY] | | | | |
| SAMPLE IMMOBILIZATION METHOD | SUITABLE | FROZEN | FROZEN | – |
| SAMPLE STORAGE TEMPERATURE | SUITABLE | A1 to A2 °C | a °C | – |
| TEST SAMPLE SIZE | SUITABLE | B1 to B2 mm$^2$ | b mm$^2$ | – |
| NUMBER OF COLLECTED CELLS | SUITABLE | > C cells | – | c cells |
| PERCENTAGE OF SEPARATED CELLS | SUITABLE | > D% | – | d% |
| PERCENTAGE OF TARGET CELLS | SUITABLE | > E% | – | e% |

FIG. 3

|  | JUDGMENT RESULTS | REFERENCE VALUES | EXAMINATION RESULTS FOR SECOND TEST SAMPLE | EVALUATION RESULTS FOR INDIVIDUAL CELLS | EVALUATION RESULTS FOR LIBRARY |
|---|---|---|---|---|---|
| [PATHOLOGICAL SUITABILITY JUDGMENT] | | | | | |
| 2001 NUMBER OF CANCER CELLS | SUITABLE | x1 | x2 | – | – |
| 2002 PERCENTAGE OF CANCER CELLS | SUITABLE | y1 | y2 | – | – |
| 2003 STAGING | SUITABLE | z1 | z2 | – | – |
| [CRITERIA FOR JUDGING TEST METHOD SUITABILITY] | | | | | |
| 2004 SAMPLE IMMOBILIZATION METHOD | SUITABLE | FROZEN | FROZEN | – | – |
| 2005 SAMPLE STORAGE TEMPERATURE | SUITABLE | A1 to A2 °C | a °C | – | – |
| 2006 TEST SAMPLE SIZE | SUITABLE | B1 to B2 mm² | b mm² | – | – |
| 3001 NUMBER OF COLLECTED CELLS | SUITABLE | > C cells | – | > c cells | – |
| 3002 PERCENTAGE OF SEPARATED CELLS | SUITABLE | > D% | – | > d% | – |
| 3003 PERCENTAGE OF TARGET CELLS | SUITABLE | > E% | – | > e% | – |
| 4001 AMOUNT OF DNA | SUITABLE | F ng | – | – | f ng |
| 4002 LEVEL OF DNA | SUITABLE | G ng/uL | – | – | g ng/uL |
| 4003 LENGTH OF DNA FRAGMENT | SUITABLE | H bp | – | – | h bp |

EXAMINATION SYSTEM, EXAMINATION DEVICE, AND EXAMINATION METHOD FOR TESTING SAMPLE QUALITY PRIOR TO BIOMARKER DETECTION

CROSS-REFERENCE TO RELATED APPLICATIONS

This application is a U.S. National Stage entry of PCT Application No. PCT/JP2015/068114, filed on Jun. 24, 2015, the entire contents of which are hereby incorporated by reference.

TECHNICAL FIELD

The present invention relates to examinations of biological samples. In particular, the present mention relates to analyses of biological tissues including gene analyses and cell function analyses, diagnoses of diseases, drug discoveries, and the like.

BACKGROUND ART

Biomarkers such as types or amounts of protein or mRNA and imitations of genes on the genome are important indicators characterizing individuals or tissues. For example, observation of cells by a pathologist is the dominant diagnostic modality for diagnosis of cancers; however, use of these biomarkers has remarkable features that objective indicators are provided and that minute changes which cannot be detected using conventional diagnostic imaging, such as partial change of a protein molecule or nucleic acid molecule which cannot be distinguished with a cell image alone can be detected.

Diagnosis using these biomarkers is important particularly for response evaluation or dose determination of recent target molecule-specific drugs in genomic drug discoveries. With these biomarkers used as indicators, it is expected that provision of medical treatment that is more appropriate for individual patients and reduction of medical expense by avoiding unnecessary treatment will be promoted. Highly sensitive detections of biomarkers are useful for early diagnosis as well as detection of subtle differences between specimens, and it is thus important to increase the sensitivity of biomarker detection techniques for medical and industrial applications.

On the other hand, considering, individuals and tissues from the viewpoint of cell biology, they are collections of diverse cells of different cell types or at different differentiation states. For example, blood cells are made up of various cell types such as erythrocytes, lymphocytes and T cells. Further, T cells, which are immune cells, have different antigen responsiveness. Taking tumor tissue as an example, cancer tissue is a collection of normal cells and cancerous cells, and it is known that genomic abnormalities are diverse rather than uniform among individual cancer cells. In other words, when samples are taken from a subject as targets to be observed, these samples are collections of diverse cells and their composition and state vary depending on the site and time at which they are collected.

As methods for analyzing gene expression information, various techniques are used depending on purposes, such as quantitative PCR, microarrays, or nucleotide sequence analysis using a massively parallel sequencer. It should be noted, however, even though different techniques are used to detect genes, it is common among comparisons of samples using these conventional methods that the diversity of the cells making up of the samples is not considered, and characteristic values are obtained by comparative analysis of values of gene expression level detected for test samples, that is, averages in cell populations making up of the test samples. When the percentage of the target cell type in the samples to be analyzed is sufficiently high, it is possible to obtain characteristic values even using a conventional method, but when the percentage of the target cells is low, the technique lacks the validity.

More specifically, when samples are compared using the above-described conventional methods, it is difficult to detect a biomarker with high sensitivity because characteristic values originating from a small number of target cells are swamped by characteristic values originating from a majority of other cells. For example, assuming tumor tissue, it is common that the percentage of cancer cells in the tumor tissue is 50% or less. Furthermore, in recent years, findings suggesting the presence of cancer stem cells estimated to be a few percent or less in the diverse cancer cells have been obtained, and it was difficult to detect biomarker possessed by such cancer stem cells. As another example assuming analysis or evaluation of iPS cells whose induction rate is several percents to 20%, a characteristic value of the iPS cells that are present low percentage would possibly be overlooked by a conventional method using averages of samples.

As a method to solve the aforementioned problem, researches on techniques for obtaining characteristic of a small number of its by separately analyzing individual cells have been under way. These are techniques for analyzing genome, gene expression, and protein of biological tissues made up of a large number of cells by focusing on differences in genome, gene expression and amount of proteins in individual cells, and called a single cell analysis technique. The single cell analysis technique has begun to be recognized to be important as a technique for improving the detection sensitivity of biomarkers by using a single cell or a small number of cells as a unit of target samples to be measured.

Under such circumstances, as shown in, for example, Non-patent literature 1, a method of creating a cDNA library (a cDNA population including all cDNAs) by changing almost all mRNA urn cDNA and immobilizing it onto beads and using it for quantification analysis has been invented. In this technique, it has been shown that repetitive use of a cDNA library can prevent the decrease in the number of molecules of slightly expressed genes due to division of a sample and allow accurate measurement of the expression level of multiple genes in one cell.

PRIOR-ART

Non-Patent Literature

Non-patent literature 1: Nature Method vol. 6, no. 7, 503-506 (2009)

SUMMARY OF THE INVENTION

Problems to be Solved by the Invention

As described above, since tissues and specimens are made up of a collection of various types of cells, a single cell analysis technique for individually analyzing cells is useful for sensitive detection with a biomarker. However, no matter how accurately a biomarker is detected in one cell, a detected value is insufficient for grasping the state of tissues and specimens, when the grasping is the original purpose. This is because an analytical result on one cell represents a characteristic value of the cell and it is remarkably inappropriate to use the analytical result on one cell as a direct measure of evaluation of a tissue which is a population of various cells.

Therefore, it is desirable to analyze as many cells as possible on a single-cell basis and integrate the analysis results as a characteristic value of tissue having diversity. The number of cells usually used by conventional analytical techniques targeting a group of cells is $10^3$ to $10^6$. Although it may be considered to improve the validity of the result of single cell analysis by performing single cell analysis repeatedly until the number of cells is almost equal to that in cell population analysis, but the single cell analysis technique is directed to analyze cells individually, so that an increase in the number of cells directly leads to an increase in cost, effort, and time for analysis.

With respect to the conventional problems as described above, an object of the present invention is to achieve biomarker detection with high accuracy while suppressing cost, effort, and time for analysis.

Means to Solve the Problems

An aspect of the present invention to solve at least one of the aforementioned problems has a configuration including: optically obtaining characteristic values of a plurality of biological samples from a specimen; comparing the characteristic values with examination information associated with the same specimen obtained in advance; and calculating an indicator to determine, based on a result of the comparison, whether a process is continued to genetic analysis of the biological samples or a re-preparation of samples from the same specimen is performed.

Effects of the Invention

The present invention has made it possible to achieve more reliable biomarker detection by ensuring validity through appropriate selection of samples to be examined while reducing cost, effort, and time for analysis in single cell analysis or analysis of a group of a small number of cells.

EMBODIMENTS FOR CARRYING OUT THE INVENTION

An example of an embodiment of the present invention is described below with reference to the drawings. This is, however, merely an example for achieving the present invention, and does not limit the present invention. Furthermore, in this embodiment, gene expression analysis using a next generation sequencer is given as an example, but the present invention also includes cases where other methods such as quantitative PCR and microarrays are used as a method of detecting genes. Similarly, gene expression analysis is also an example of a biomarker derived from individual cells, and includes cases where a detection target is a nucleic acid molecule such as miRNA or genomic DNA or protein, or a metabolite of cells.

In this embodiment, a specimen is a sample derived from a certain subject to be examined. Even if samples are derived from a common subject, the samples obtained, for example, at different sites, at different times, or by different methods are regarded as different samples. Furthermore, in this embodiment, a portion of a specimen prepared by collecting a portion of a sample by, for example, section slicing or laser micro-dissection, or concentrating, for example, certain cells using a cell sorter or the like is especially defined as a test sample. For example, samples collected by biopsy are specimens, and paraffin-embedded sections used for pathological observation of these specimens are test samples.

One of the major differences of this embodiment from conventional techniques for detecting biomarkers lies in that the embodiment aims at performing biomarker detection with higher accuracy in consideration of the aforementioned diversity of cells and tissues. That is, even if test samples are derived from a common specimen, different test samples are not exactly the same cell populations. Judgment in consideration of the difference between these test samples is important for techniques of highly sensitive biomarker detection. For example, in a histological examination in cancer diagnosis, microscopic observation of paraffin-embedded sections of an test sample is performed by a pathologist. When the pathologist judges from the observation result that an additional analysis with a biomarker such as genetic analysis is required, the specimen is then subjected to biomarker detection. At this time, since the test samples used for the biomarker detection are sections next to the paraffin-embedded sections previously subjected to the microscopic examination, they are different from the previously observed samples in terms of spacious position in the sample even though derived from a common specimen.

This embodiment describes a single cell analysis and examination system, a single cell analysis and examination device, and a method for single cell analysis and examination, which are implemented, sufficiently considering possibility that test samples for microscopic observation and test samples for biomarker detection are different from each other in percentage and diversity of cancer cells because different test samples are used.

Selection of samples to be subjected to biomarker detection is a significant challenge. Considering the diversity of tissues and cells, since specimens of tissue collected at different sites or different times are differently diverged, analysis of appropriate samples in consideration of their diversity is important. First of all, prior to the description of an exemplified system configuration of this embodiment, the importance of sample selection is described by taking cancer tissue as an example.

It is known that cancer tissue is a collection of normal cells and cancerous cells and diversity exists even among cancer cells. Furthermore, the percentage of normal cells and cancer cells in one tumor tissue varies depending on sites in the tumor. Accordingly, when aiming at grasping the nature of a cancer tissue in detail, it is required to: i) prepare samples from multiple sites of the tumor tissue, ii) analyze the samples at a single-cell level, and iii) integrate the results of the analysis for these tissue fragments. When, however, the sample to be analyzed lacks validity such as a region where the percentage of cancer cells in tumor tissue is extremely low, the results of the analysis would be a cause of an incorrect judgment. In other words, considering that cells and tissues are essentially diversified populations, it is extremely important to judge the validity of test samples in highly sensitive detection of biomarkers using a single cell analysis technique.

Figure 5:
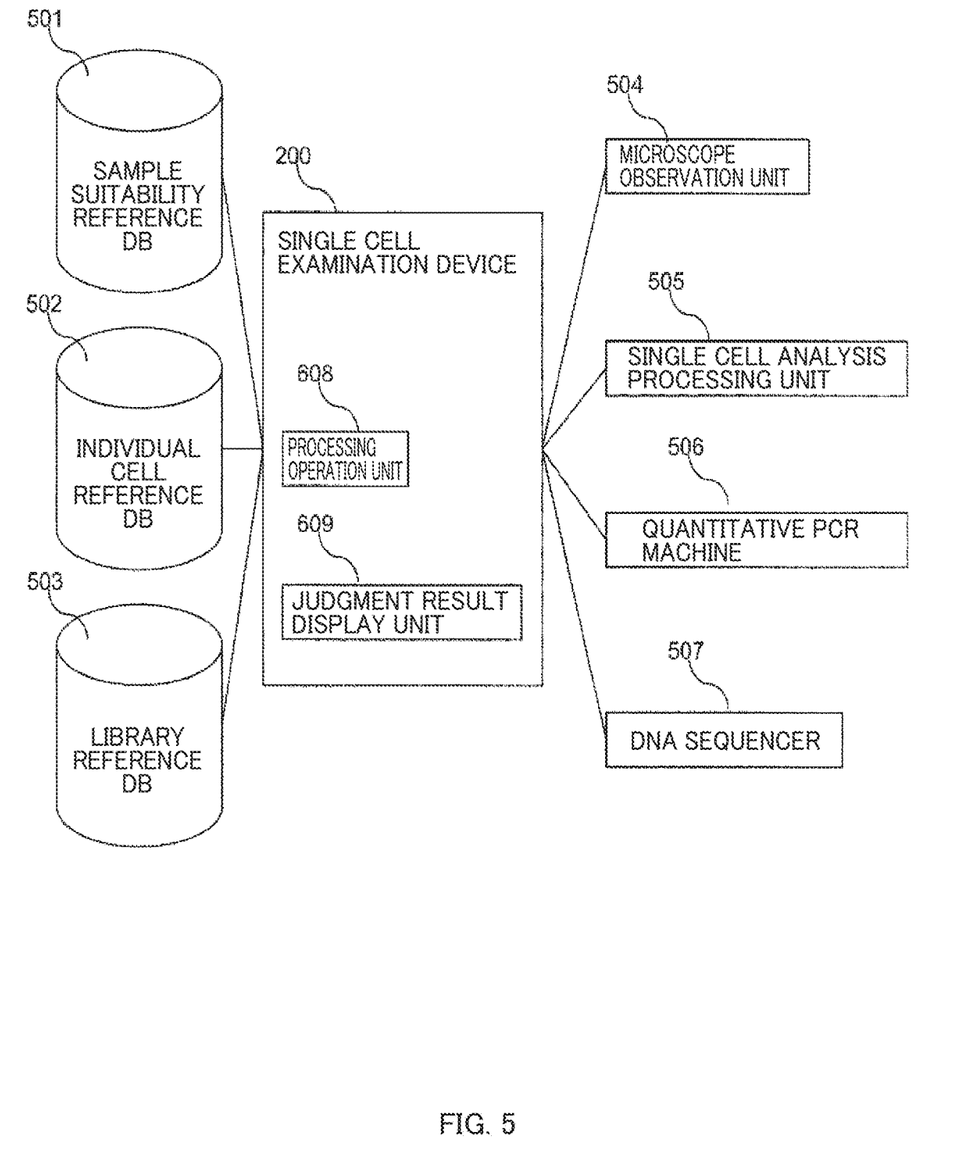
FIG. 5 A block configuration diagram showing an example of a configuration of a single cell analysis and examination system.

Based on such importance of determining the validity of test samples, an exemplified configuration of a single cell analysis and examination system in this embodiment is described with reference to FIG. 5. The system includes a sample suitability criteria database 501, an individual cell criteria database 502, a library criteria database 503, a microscope observation unit 504 for observing cells, a single cell analysis processing unit 505 for preparing separate cells, a quantitative PCP machine 506 for performing quantitative PCR, a DNA sequencer 507 for analyzing nucleotide sequences of the produced DNA library, and a single cell examination device 200 that can be connected to them.

Furthermore, the single cell examination device 200 includes a processing operation unit 608 and a judgment result display unit 609. As will be described later with reference to FIG. 1, the processing operation unit 608 refers to at least one of the sample suitability criteria database 501, the individual cell criteria database 502, and the library criteria database 503, and performs a processing operation and a judgment operation by comparing the referred database(s) and each examination value. Furthermore, the judgment result display unit 609 displays results of processing and judgment performed by the processing operation unit 608.

As will be described in detail with reference to FIG. 2, the sample suitability criteria database 501 stores criteria based on results of a detailed examination judgment 102 performed in advance using test samples derived from a common specimen, and conditions for the samples determined by the results of a sample suitability judgment 201 and the applied biomarker examination technique.

As will be described in detail with reference to FIG. 3, the individual cell criteria database 502 stores criteria based on results of an individual cell evaluation 204 and conditions for the samples determined by the applied biomarker examination technique.

As will be described in detail with reference to FIG. 4, the library criteria database 503 stores criteria based on the results of the individual cell evaluation 204 and conditions for the samples determined by the applied biomarker examination technique.

While this embodiment illustrates the sample suitability criteria database 501, the individual cell criteria database 502, and the library criteria database 503 as separate databases, these databases may be configured in one storage medium.

This system achieves specimen evaluation/analysis in consideration of the diversity of tissues and cells which was difficult to achieve in the past, and it is also possible to make a system in which a part or a plurality of these devices and databases are connected.

Next, an example of a process flow of the present system is described with reference to FIG. 1. This system performs the following operations in order to evaluate specimens from the results of highly sensitive biomarker detection analysis with significant consideration of the diversity of cells and tissues. Furthermore, an operation to which or from which steps are added or removed as necessary is performed.

Prior to the operations performed by the present system, test samples are prepared in advance from a specimen (101), and a pathologist, an inspector or the like determines, from the test results for these test samples (102), whether or not a detailed examination necessary. Test samples to be subjected to the detailed examination are then prepared (103). After that, the system performs the following operations.

First, the sample suitability judgment 201 by the single cell analysis and examination device 200 is described. As described above, since the test samples used for the detailed examination necessity judgment 102 are not the same as the test samples to be subjected to the biomarker detection, the single cell examination device 200 performs a sample suitability judgment 201 on a sample prepared in test sample preparation 103 after the detailed examination judgment 102. In the sample suitability judgment 201, observation by the microscope 504 or the like, for example, is performed on the samples prepared in the test sample preparation 103 to be subjected to the biomarker examination, and the processing operation unit 608 refers to the sample suitability criteria database 501 for the observation result and compares the observation result with a examination result in the detailed examination necessity judgment 102 that precedes to check their suitability. It then presents an indicator of continuation of the process or re-preparation of test samples on the judgment result display unit 609.

In the sample suitability judgment 201, results of the detailed examination judgment 102 performed in advance using the test samples derived from the same specimen are important indicators, because since each of the test samples is a group of cells having its own characteristics when considering the diversity of biological tissues and cells, it is reasonable to compare the test samples derived from a common specimen rather than to determine uniform criteria for sample suitability judgment. The examination of samples performed in sample suitability judgment 201 may use the same method as the prior detailed examination judgment 102, but since it is desirable that the examination does not interfere with the detailed biomarker examination to be performed subsequently, the sample suitability judgment is performed using a different method such as detection of certain antigen by immunostaining. Raman image observation or phase contrast microscope that is less invasive to samples. In the case where the two judgment methods are different, criteria for correlating the results of the observation performed using either method are established. These criteria are stored in the sample suitability criteria database 501 as reference information for the sample suitability judgment. In more detail, in the sample suitability judgment 201, the processing operation unit 608 judges whether the examination is to be continued or the re-preparation in the test sample preparation 103 is performed by referring to the results of the detailed examination judgment 102 on the samples derived from the same specimen and the results of the examination in the sample suitability judgment 201 corresponding to the judgment results.

Figure 2:
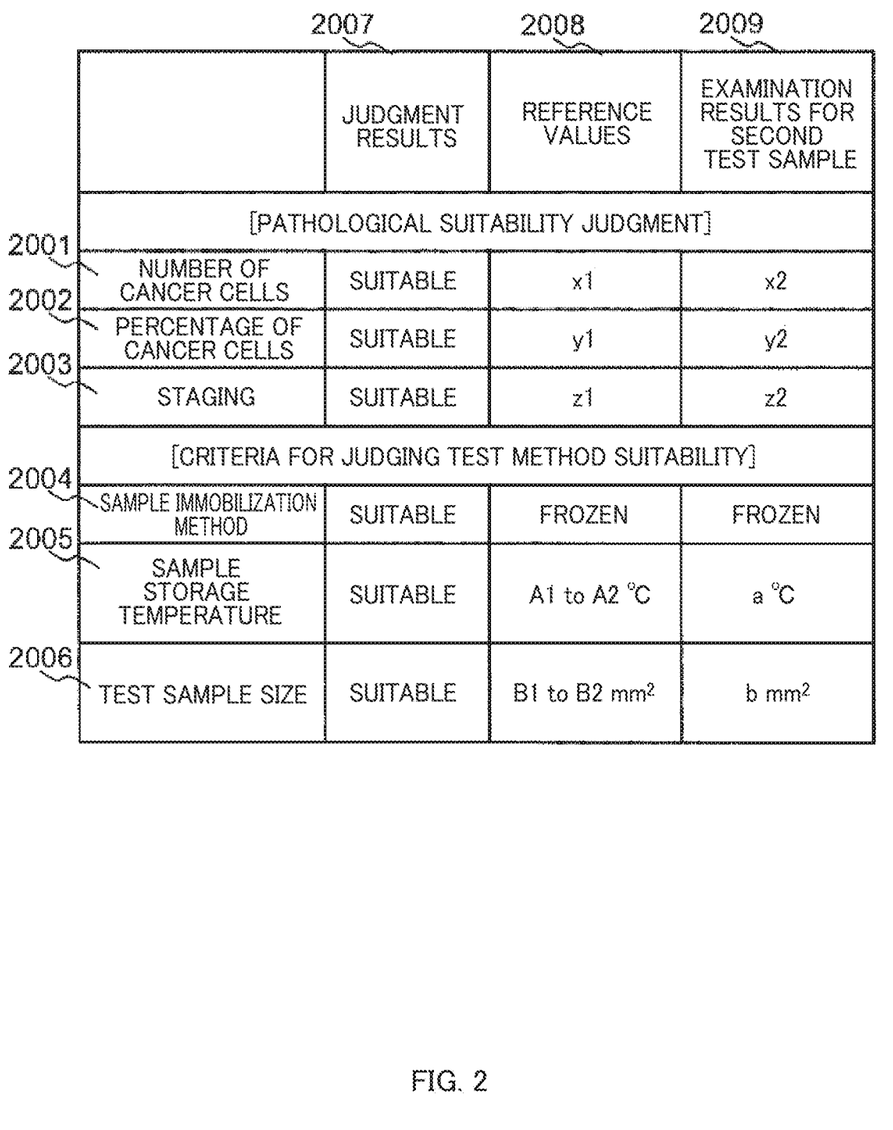
FIG. 2 A diagram showing an example of information stored in a sample suitability criteria database.

With reference to FIG. 2, an example of information stored in the sample suitability criteria database 501 used for the sample suitability judgment 201 is described. The sample suitability criteria database 501 store, as criteria 2008, criteria for pathological suitability judgment such as the number of cancer cells 2001, the percentage of cancer cells 2002, and staging 2003 in the results of a first test sample preparation 101.

The sample suitability criteria database 501 also stores, as the criteria 2008, criteria for judging suitability of the test method such as a sample immobilization method 2004, a sample storage temperature 2005, and a test sample size 2006 in addition to the criteria form pathological suitability judgment. They are indicators that can be used for judging the level of the samples required in the next step, cell separation 203, and serve as a criteria for suitability of the test samples to be judged.

The processing operation unit 608 judges the suitability of the test samples by comparing examination results 2009 of a second test sample preparation 103 with the criteria 2008 and records the judgment result 2007.

Here, the items described in association with the tumor tissue are exemplified in FIG. 2, but these items are examples and names and meaning of the items are criteria for the pathological suitability judgment corresponding to the examinations performed in the first test sample preparation 101. As the criteria for the pathological suitability judgment in the sample suitability criteria database 501, observation results for the test samples obtained by the first test sample preparation 101 used in the detailed examination judgment 102 and results (2001 to 2003) of observation performed, for example, using the microscope 504, on the examination samples in the second test sample preparation 103 which are subjected to the biomarker examination, are stored in such a manner that the criteria 2008 and the examination results 2009 can be compared with each other.

As described above, a test that allows sample suitability judgment is performed for the second test sample preparation 103. The result is stored in the examination result 2009 of the sample suitability criteria database 501, and then the judgment results 2007 for the suitability of the test samples are stored by comparing the examination results for the two test samples.

It should be noted that the judgment criteria in each of the databases 501, 502, and 503 as well as the sample suitability criteria database 501 can be improved by learning. For example, the databases may be configured such that the criteria 2008 are varied based on the evaluation results in each of the judgment/evaluations (201, 204, and 207) in FIG. 1.

In addition, since the test samples prepared in the second test sample preparation 103 are to be subjected to precise biomarker detection, a desirable sample condition is defined according to the examination technique performed based on the criteria for judging the suitability of the test method. The sample immobilization method 2004, the sample storage temperature 2005, the test sample size 2006, and the like illustrated in FIG. 2 are items that greatly affect the results of the biomarker examination, and it is important to compare and judge the suitability of the items affecting these examination values with the indicators stored in the sample suitability criteria database. With some or all of the examination results used for judging the suitability among the test samples, and the conditions of the test samples defined by the biomarker detection technique, and the results of the suitability judgment made by the present system being able to be compared and browsed, they are presented, on the judgment result display unit 609, to users of this system as indicators for determining continuation of the operations.

The sample suitability judgment 201 performed by the single cell analysis and examination device 200 of this system makes it possible to ensure the validity of the prepared samples, that is, the validity of the examination results by judging the suitability criteria for the test samples through the suitability judgment of the samples subjected to biomarker detection performed as detailed examination with reference to the results for the test samples derived from the same specimen, and repeating, if the suitability criteria are not satisfied, an instruction to re-prepare samples until the suitability criteria are satisfied.

Furthermore, it can be assumed that test samples satisfying all of the suitability criteria cannot be obtained because they are prepared from a limited number of specimens. In such a case, it is also possible to compromise for one or more suitability criteria to perform subsequent examinations. Even in such a case, the present system makes it possible to contribute to improvement of the accuracy of judgment for the examination results by clarifying the state, relative to the suitability criteria, of the test samples subjected to the examination or suitability indicators that deviate from the criteria.

Figure 1:
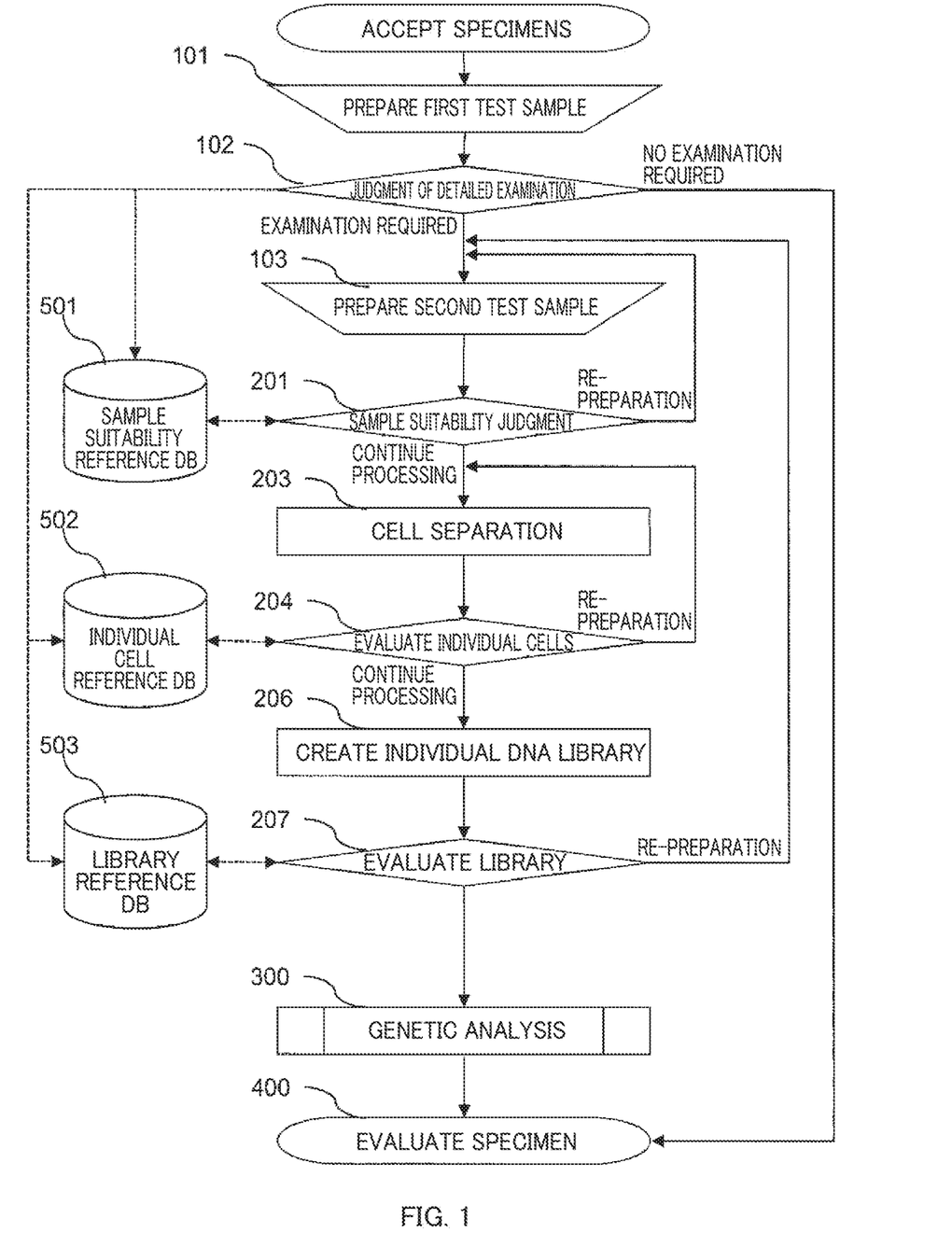
FIG. 1 A flow-chart representing a process of a single cell analysis and examination system.

Next, the individual cell evaluation 204 by single cell analysis and examination device 200 in FIG. 1 is described. In the individual cell evaluation 204, the single cell analysis and examination device 200 performs evaluation on the individual cells having undergone the cell separation 203. The cells prepared by the cell separation 203 for the test samples for which continuation of the process has been determined by the sample suitability judgment 201 are targeted for the individual cell evaluation 204.

Here, the cell separation 203 is a pre-processing for enabling individual cells to be examined. Therefore, in the cell separation 201, either a technique of separating cells by merely detaching the adhesion between cells, or a technique of separating certain cells using a cell sorter or laser microdissection, or the like may be used. In any case, cells are prepared by a method suitable for biomarker detection to be performed.

The individual cell evaluation 204 performed by this system consists of observation of separated individual cells and evaluation of the observation results. The observation of cells may be performed either by the single cell analysis processing unit 505 or by the microscopic observation unit 504 and is an operation of evaluating individual cells on the results obtained by performing the cell separation step by the processing operation unit 608.

Figure 3:
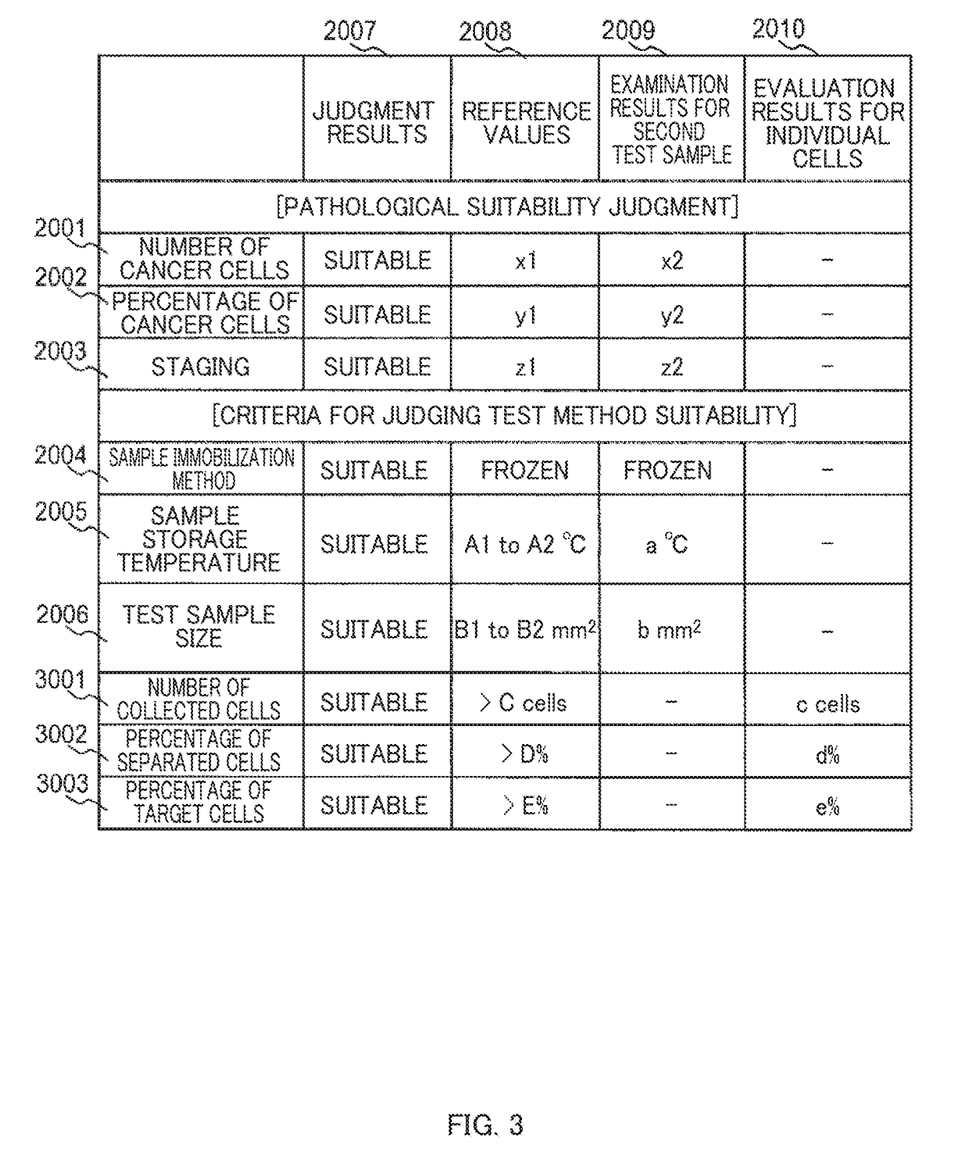
FIG. 3 A diagram showing an example of information stored in an individual cell criteria database.

With reference to FIG. 3, described is an example of examination item information stored in the individual cell criteria database 502 which is referred to and used for the individual cell evaluation 204 by the processing operation unit 608. In the individual cell criteria database 502, results, of the examinations using the first test sample preparation 101 and examination results of the sample suitability judgment 201 are stored. In FIG. 3, the items described in association with the tumor tissue are exemplified, but these items are merely examples, and the names and meaning of the items correspond to the examination made in the first test sample preparation 101. In this embodiment, the sample suitability criteria database 501 and the individual cell criteria database 502 are described as independent databases, but these reference databases may be on the same storage medium.

In the individual cell evaluation 204 performed by the single cell analysis and examination device 200 of the present system, the validity relative to the results of the sample suitability judgment 201 is evaluated by the processing operation unit 608 for the samples after the cell, separation and at the same time the condition of the test samples essential for the analysis of the biomarker detection results for the individual cells which is performed in a subsequent process is evaluated.

Examples of information used as criteria for the individual cell evaluation 204 stored in the individual cell criteria database 502 include the number of collected cells 3001, a percentage of separated cells 3002, and a percentage of target cells 3003. Among these indicators, the cell size 2006 and the like are judgment criteria determined by referring to the results of the sample suitability judgment depending on the test samples. In addition, the individual cell criteria database 502 stores judgment criteria determined by the examination technique in individual biomarker detection, such as the percentage of separated cells 3002 and the percentage of target cells 3003 such as criteria that "the number of cells is equal to or larger than 1000 and a percentage of the cells that have been insufficiently individualized is 5% or less."

In the individual cell criteria database 502, evaluation results 2010 for the reference information such as the number of collected cells 3001, the percentage of separated cells 3002, and the percentage of target cells 3003 are stored in such a manner that they can be compared with the criteria 2008. The processing operation unit 608 determines the suitability by comparing the individual cell evaluation results 2010 with the criteria 2008 for reference information such as the number of collected cells 3001, the percentage of separated cells 3002, and the percentage of target cells 3003 and records the judgment results 2007.

The judgment result display unit 609 presents, to users of this system, the results of the judgment performed by the processing operation unit 608 using the reference information shown in FIG. 3. If the judgment criteria, shown in FIG. 3, such as the number of collected cells 3001, the percentage of separated cells 3002, and the percentage of target cells 3003 are satisfied in the individual cell evaluation 204, information recommending continuation of the process is displayed. Conversely, if the results do not conform to the judgment criteria, information indicating that re-preparation of the cells for the cell separation step 203 using the samples satisfying the sample suitability judgment 201 is necessary is displayed on the judgment result display section 609. This operation makes it possible to ensure the reliability of the entire examination by performing individual cell evaluations repeatedly until the individual cell evaluation criteria are satisfied.

Like the sample suitability judgment 201, it can also be assumed that a test sample that satisfies all of the suitability criteria stored in the individual cell criteria database 502 cannot be obtained. In such a case, it is also possible to select one or more suitability indicators to perform subsequent examinations. Even in such a case, the present system makes it possible to contribute to improvement of the judgment accuracy of examination results by clarifying the suitability reference state of the test samples subjected to the examination.

Next, library evaluation 207 by the single cell analysis and examination device 200 is described. For test samples for which continuation of the process has been determined in the individual cell evaluation 204, each cell is subjected to pre-processing before the biomarker detection. For example, in the case of genetic analysis, DNA library preparation 206 is performed for individual cell. In the library evaluation 207, suitability judgment to the level required for the gene analysis 300 on the prepared DNA library is performed with the single cell analysis and examination device 200.

An example of examination item information stored in the library criteria database 503 used for the library evaluation 207 is described with reference to FIG. 4. The library criteria database 503 stores the results of the examinations performed using the first test sample preparation 101, the examination results of the sample suitability judgment 201, and the examination results of the individual cell evaluation 204. In FIG. 4, items described in association with the tumor tissue are exemplified, but these items are merely examples and names and meaning of the items correspond to the examinations made in the first test sample preparation 101.

The library evaluation 207 performed by the single cell analysis and examination device 200 of this system is based on the criteria determined by the analytical technique used for gene analysis 300 in addition toile conventional judgment criteria in the sample suitability judgment 201 and the individual cell evaluation 204. For example, the criteria determined by the analytical technique used for the gene analysis 300 are, for example, DNA amount 4001, DNA concentration 4002, and length of DNA fragment 4003.

Evaluation indicators for these DNA libraries are acquired using the single cell analysis processing unit 505 or the quantitative PCR machine 506, and the judgment result display unit 609 presents the examination results together with the judgment indicators to the user of the present system.

In the library criteria database 503, the evaluation results 2011 are stored in such a manner that they can be compared with the criteria 2008 for the reference information such as DNA amount 4001, DNA concentration 4002, and length of DNA fragment 4003. The processing operation unit 608 judges the suitability by comparing the individual cell evaluation results 2011 with the criteria 2008 for the reference information such as DNA amount 4001, DNA concentration 4002, and length of DNA fragment 4003 and records the judgment results 2007.

Figure 4:
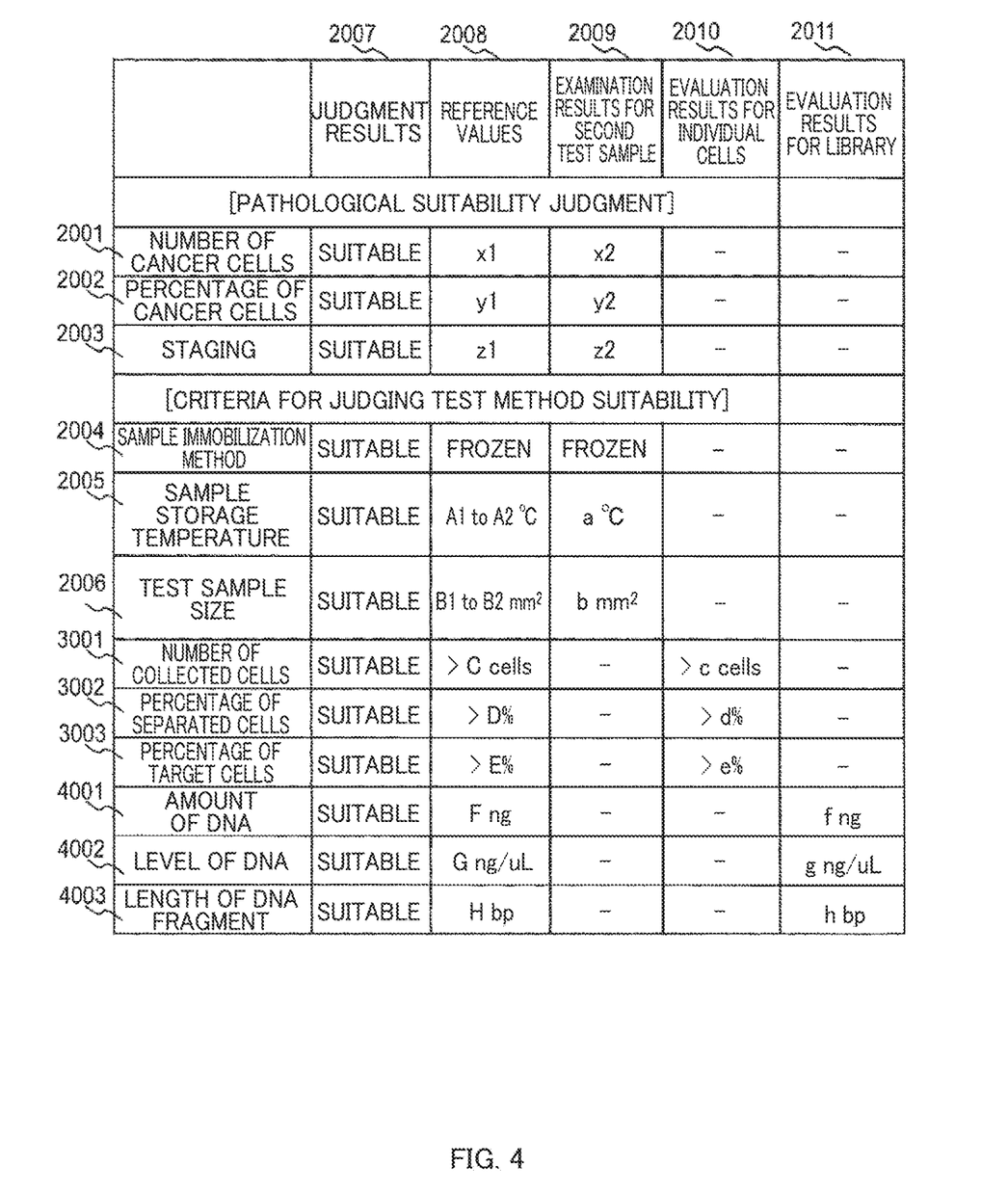
FIG. 4 A diagram showing an example of information stored in a library criteria database.

The judgment result display unit 609 presents, to users of this system, the results of the judgment performed by the processing operation unit 608 using the reference information as shown in FIG. 4. If the judgment criteria such as DNA amount 4001, DNA concentration 4002, and length of DNA fragment 4003 as shown in FIG. 4 are satisfied in the library evaluation 207, information recommending continuation of the process to specimen evaluation 300 based on the gene analysis 300 is displayed. Conversely, if they do not conform to the judgment criteria, information recommending re-preparation to the cell separation step 203 with the samples satisfying the sample suitability determination 201 is displayed.

The library evaluation 207 of the present system greatly contributes to ensuring reliability of the examination, and reducing cost, effort, and time for examination like the case of the individual cell, evaluation 204 described above. Although it is desirable that the library evaluation 204 is performed on individual cells in the examination of them, it is also possible to reduce the examination cost and the number of steps for examination by performing the library evaluation 204 using averages of all cells or sampling examinations using some representative cells.

The examinations using a single test sample has been described with reference to FIGS. 1 to 4. As described above, by analyzing results of biomarker detection in individual cells in consideration of the detailed examination judgment 102, the sample suitability judgment 201, the individual cell evaluation 204, and the library evaluation 206, specimen evaluation 400 in consideration of the diversity of cells and tissues can be achieved, which was difficult to achieve in conventional arts.

However, in order to understand the details of tissue having diversity, it is desirable to examine a plurality of test samples. This system can be applied to individual test samples and then integrate and provide their evaluation results. Although the suitability judgment and the individual cell evaluation performed on each test sample are as described above, the system may be configured such that these examinations and evaluations are performed individually on each of the n test samples by the processing operation unit 608 of the single cell analysis and examination device 200 and the examination results for the specimen samples with which reliability indicators are associated are integrated by the processing operation unit 608 and presented on the judgment result display unit 608 as the examination results for the specimen. For example, the system may be configured such that examination results of n test samples are integrated in a database and presented on the judgment result display unit 608 for at least a part of the judgment results 2007, the criteria 2008, the second test sample examination results 2009, the individual cell evaluation results 2010, and the library evaluation results 2011 in FIG. 4.

Fields to which this system can be applied include medical and pharmaceutical development fields such as observation of cancer tissue, analysis of blood cells, and evaluation of cultured cells related to regenerative medicine. It is possible to provide new biomarker information for these important fields with higher reliability which was impossible in the conventional art. Furthermore, continuation of analysis on the sample to be analyzed and presentation of indicators for re-preparation of the sample are performed during the course a the analysis, so that examination with poor reliability can be prevented and reduction in examination cost can be achieved.

As described in this embodiment, it is extremely important in assuring the reliability of examinations to perform the evaluation of individual cells prepared for single cell analysis prior to detection of individual biomarkers such as gene analysis, and this contributes greatly to reduction in cost, effort, and time for examination. This is because the biomarker detection by genetic analysis and immunoassay on individual cells requires more cost, effort, and time for examination compared with conventional techniques for examining cell populations. As in this embodiment, by judging the validity of the test sample determined from the examination result of the same specimen and the validity as a sample used for the biomarker examination in a preliminary stage of the process where the largest cost, effort, and time occur. By doing so, efficient examination can be performed.

DENOTATION OF SYMBOLS

200 . . . single cell analysis and examination device, 201 . . . sample suitability judgment, 204 . . . individual cell evaluation, 206 . . . library evaluation, 501 . . . sample suitability criteria database, 502 . . . individual cell criteria database, 503 . . . library criteria database, 504 . . . microscope observation unit, 505 . . . single cell analysis processing unit, 506 . . . quantitative PCR machine, 507 . . . DNA sequencer, 608 . . . processing operation unit, 609 . . . judgment result display unit

The invention claimed is:

1. An examination method for examining test quality for cancer diagnoses, the method comprising:

storing, in a database, examination information of a first biological sample prepared from a cancer tissue specimen for diagnosis of the cancer tissue obtained in advance as judging test method suitability criteria, the judging test method suitability criteria comprise a sample immobilization method reference value, a sample storage temperature reference value, and a test sample size reference value;

obtaining examination results of a second biological sample prepared from the same cancer tissue specimen, the examination results of the second biological sample comprising a sample immobilization method, a sample storage temperature, and a test sample size associated with the second biological sample;

comparing, using a processor, the examination results of the second biological sample against the judging test method suitability criteria;

generating, using the processor, an indicator to determine whether a process is continued to perform biomarker detection of the second biological sample or to re-prepare a biological sample from the cancer tissue specimen, based on a result of comparing the examination results of the second biological sample against the judging test method suitability criteria, wherein the indicator indicates performance of biomarker detection of the second biological sample when the examination results of the second biological sample are deemed suitable by matching the sample immobilization method reference value and being within a range of the sample storage temperature reference value and the test sample size reference value, and the indicator indicates re-preparation of a biological sample from the cancer tissue specimen when one of the examination results of the second biological sample is deemed not suitable by not matching the sample immobilization method reference value or being outside of the range of the sample storage temperature reference value or the test sample size reference value;

determining to re-prepare a biological sample based on the determined indicator indicating re-preparation of a biological sample;

iteratively re-preparing the second biological sample prepared from the same cancer tissue specimen and generating the indicator for the re-prepared second biological sample while the indicator indicates the re-preparation of the biological sample; and performing biomarker detection of the re-prepared second biological sample after the iterative re-preparing of the second biological sample once the indicator indicates performance of biomarker detection of the re-prepared second biological sample.

2. The examination method according to claim 1, wherein performing biomarker detection of the re-prepared second biological sample comprises a step of cell separation and a step of creating an individual cell DNA library.

3. The examination method according to claim 2, further comprising, upon performing the step of cell separation, presenting an indicator to determine whether re-preparation of the individual cells is performed, based on comparison of one or more cell evaluation results selected from a group of cell evaluation results consisting of a number of collected cells, a percentage of separated cells, and a percentage of target cells with the judging test method suitability criteria, wherein the judging test method suitability criteria further comprise a reference number of collected cells, a reference percentage of separated cells, and a reference percentage of target cells, wherein the comparison of the one or more cell evaluation results with the judging test method suitability criteria comprises determining whether the one or more cell evaluation results exceed the reference number of collected cells, the reference percentage of separated cells, and the reference percentage of target cells.

* * * * *